(12) United States Patent
Clarke

(10) Patent No.: US 8,114,332 B2
(45) Date of Patent: Feb. 14, 2012

(54) INJECTION MOULDING METHOD

(76) Inventor: Peter Reginald Clarke, Petworth (GB)

( * ) Notice: Subject to any disclaimer, the term of this patent is extended or adjusted under 35 U.S.C. 154(b) by 0 days.

(21) Appl. No.: 12/523,049

(22) PCT Filed: Jan. 10, 2008

(86) PCT No.: PCT/GB2008/000072
§ 371 (c)(1),
(2), (4) Date: Dec. 11, 2009

(87) PCT Pub. No.: WO2008/084230
PCT Pub. Date: Jul. 17, 2008

(65) Prior Publication Data
US 2010/0092706 A1   Apr. 15, 2010

(30) Foreign Application Priority Data
Jan. 12, 2007   (GB) .................................. 0700641.4

(51) Int. Cl.
*B29C 45/56* (2006.01)
(52) U.S. Cl. .................................... 264/328.7; 264/40.5
(58) Field of Classification Search ............... 264/328.1, 264/328.7, 40.5
See application file for complete search history.

(56) References Cited

U.S. PATENT DOCUMENTS

| | | | | |
|---|---|---|---|---|
| 4,071,532 A | * | 1/1978 | Rose | 264/328.7 |
| 4,092,385 A | * | 5/1978 | Balevski et al. | 264/45.5 |
| 4,522,778 A | * | 6/1985 | Baciu et al. | 264/328.7 |
| 5,529,483 A | * | 6/1996 | Abe et al. | 425/589 |
| 5,798,063 A | * | 8/1998 | Bender et al. | 264/45.5 |
| 6,030,573 A | * | 2/2000 | Matsumoto et al. | 264/511 |
| 6,440,351 B1 | * | 8/2002 | Saito et al. | 264/328.7 |
| 2004/0142057 A1 | | 7/2004 | Kao et al. | |
| 2005/0236740 A1 | | 10/2005 | Niewels | |

FOREIGN PATENT DOCUMENTS

| | | |
|---|---|---|
| DE | 102004003136 A1 | 9/2004 |
| EP | 0 999 023 A1 | 5/2000 |
| EP | 1 108 520 A1 | 6/2001 |
| GB | 2 138 737 A | 10/1984 |
| GB | 2445547 | 3/2010 |
| JP | 61-261018 | 11/1986 |
| JP | 07-052215 | 2/1995 |

OTHER PUBLICATIONS

International Search Reported dated Aug. 6, 2008 form PCT/GB/2008/000072.

\* cited by examiner

*Primary Examiner* — Jill Heitbrink

(57) ABSTRACT

An injection mold for injection molding an article having a base and a sidewall, the injection mold comprising: first and second mold parts which are adapted to be connected together in a closed configuration so as to define a mold cavity there between, the mold cavity having a base portion and a sidewall portion, an injector for injecting into the mold cavity molten material to be molded into the article, at least one portion of one of the first and second mold parts being movable when the first and second mold parts are in the closed configuration so as to vary the volume of the mold cavity, an actuator for selectively moving the at least one portion of one of the first and second mold parts in first and second directions so as to increase and reduce, respectively, the volume of the mold cavity.

28 Claims, 8 Drawing Sheets

INJECTION MOULDING METHOD

The present invention relates to an injection mould, to an injection moulding apparatus and to a method of injection moulding an article, or a plurality of articles. In particular, the present invention relates to the injection moulding of containers, and preforms for containers, from plastics material.

Injection moulding of articles from plastics materials, in particular thermoplastic polymers, is well known in the art. In particular, the injection moulding of containers, and preforms for containers, from plastics material is conventional in the art.

It is often desired to injection mould plastics containers having a small wall thickness, for example to reduce material costs. When it is necessary to injection mould a container having a high L/T ratio (where L is the flow length of the molten plastics material from the injection gate and T is the wall thickness), a high injection pressure at the gate is needed to ensure that the mould cavity is filled with the molten plastics material. The gate acts to restrict material flow therethrough, and the wall section directly opposite the gate also restricts the material flow into the cavity.

The conventional approach to attempt to reduce the high injection pressure at the gate is to inject the molten plastics material at a faster injection rate, and to raise the melt temperature to lower the melt viscosity, to enable the mould to be filled by the molten plastics material.

It is also well known that in order to reduce the fill pressure, it is possible when designing a container to increase the base thickness, particularly in the gate area. This gate area is also the hottest area of the injection moulding. As all of the material in the sidewall has to flow across the base, within an interior gap defined between the static exterior skin layers laid down during the first phase of filling, base cooling is always a problem. Another problem with such laminar flow across the base is that the skins are progressively solidifying and therefore getting thicker, narrowing the flow channel. This causes a further restriction on the material flow.

All of this adds up to the need to flow the molten material into the cavity at a faster rate, and to do that one needs to increase the fill pressure. The higher fill pressure will, in turn, require a higher clamp pressure to counter the hydraulic force on the end of the core. It should be readily apparent to the skilled reader why injection moulding machines for the manufacture of plastics packaging need to have very high injection speeds and pressures, and very rigid platens, to make what appears to be a simple container or preform.

Over the years a significant development in the packaging art to try to address these problems has been in increase the melt flow index of the plastics materials, while maintaining their rigidity and impact resistance. This merely required adjustment of the machine and mould specifications to suit the newer materials. In other words, some attempts to solve the high gate pressure problems discussed above of injection moulding of plastics materials into thin-walled bodies has primarily been focused on the nature of the plastics material, rather than the fundamental injection moulding processes and machines.

A particularly important application for injection moulding in the packaging industry is to make injection moulded polyester, particularly polyethylene terephthalate (PET), preforms for subsequent blow moulding into containers, typically bottles for carbonated beverages. It is understood in the art that in order to make good quality blow moulded bottles from PET injection moulded preforms, the preforms must be injection moulded with the minimum of moulded-in stress. This is because any stress pattern resulting from the preliminary injection moulding process would affect the way in which the preform stretches during the subsequent blow moulding process.

The optimum preform would have no visible signs of stress when viewed under polarised light; however, this is very difficult to achieve with conventional injection moulding techniques.

This is due to the requirement of continuing to add material to the preform as it cools during the filling and packing phases of the injection moulding cycle. Internal shrinkage causes the preform to collapse away from the mould cavity wall creating surface "ripples", which are unacceptable to the blow moulding process. To overcome internal shrinkage, it is necessary to continue to add material into the preform during this shrinkage phase. This requires the maintenance of a fill pressure and material flow sufficient to compensate for the changing density caused by the cooling of the material. However, such pressure and forced flow cause residual stress to be present in the ultimate injection moulded article.

The injection moulding of preforms requires a delicate balance of pressure and flow to achieve the low stress required to blow mould the preform into a good quality bottle.

Preforms have tended to become shorter and fatter over the years to assist in the reduction of gate stress, by attempting to avoid the higher pressures required to fill the longer and thinner wall section mouldings. Such higher pressures also tended to cause core shift, where the central core defining the preform cavity is shifted off its axis by the higher-pressure fill, which creates a wall section differential around the circumference of the preform that cannot be accommodated during the subsequent blow moulding stage.

It is also known to inject the molten plastics material before the clamp pressure has been fully applied to the injection mould, i.e. before the two mould halves have been urged together under an applied clamp force so as to fully close the mould cavity. Husky, Netstal and BMB all have this as a standard procedure in their software for operating their injection moulding machines. This effectively increases the cavity base thickness opposite the gate during the first phase of injection to improve the molten material flow. The problem with this method is that the mould loses concentricity when the mould is not fully closed. The two mould halves are normally mutually engaged by a taper lock to ensure that in the closed configuration the two mould halves are coaxial. However, the taper lock becomes ineffective to ensure concentricity before the clamp pressure has been fully applied to the injection mould, and this can cause the initially injected material to become circumferentially asymmetrically distributed within the cavity.

There is also known in the art a process of injection compression moulding (ICM) that has been proven to overcome many of these problems. In particular, the injection compression moulding process can allow increased flow-length:wall thickness ratios in injection moulded parts, and can reduce clamping forces and injection pressures, and thereby reduce internal material stresses.

There are four injection compression moulding processes.

In sequential injection compression moulding (Seq-ICM), the material is injected into the mould cavity when the mould is not fully closed. This creates a larger mould cavity portion of about twice the final wall thickness into which the injected material is received. Thereafter, the mould is closed by the clamp. This closing action causes the material to be distributed by the closing clamp pressure throughout the entire mould cavity.

In simultaneous injection compression moulding (Sim-ICM), the material is injected into the mould cavity when the mould is not fully closed, and simultaneously the mould is closed by the clamp.

In breathing injection compression moulding (Breath-ICM), the mould is fully closed before the material is injected into the mould cavity. Then the mould is progressively opened during the injection to create a larger mould cavity portion than the final wall thickness. When nearly all of the material volume has been injected, the mould is closed by the clamp. This closing action causes the material to be distributed by the closing clamp pressure throughout the entire mould cavity.

In all of these three injection compression moulding processes the mould is required to be at least partly open during the moulding process. These processes therefore encounter the coaxial non-alignment problems for the mould halves discussed above.

The present inventor has earlier devised a modified sequential injection-compression moulding process that is the subject of U.S. Pat. No. 7,090,800. This teaches the use of the core to be pushed back by the incoming material under a light spring pressure and then using the machine to clamp up to finish the flow and pack the moulding. This process used a precise shot volume control to meter the material into a variable cavity and then compress to achieve fully packed and low stress mouldings. This modified sequential injection-compression moulding process injected all of the material into the cavity volume between the end of the core and the base of the cavity. The injection pressure causes the core to be pushed back, thereby enlarging the volume, and reducing the material pressure in the cavity. Thereafter, the core is rapidly forced forwardly to reduce the volume and to displace the material to the end of cavity flow. This force comes from the machine clamp.

The inventor's earlier modified sequential injection-compression moulding process provided a number of advantages as compared to conventional injection moulding processes, in particular that the material can be processed at lower temperatures; lower clamp pressures are needed; 30% faster cycle time are achievable and very thin mouldings can be made.

However, the process also suffers from some disadvantages, in particular: there is a need to use an individual shooting pot per cavity; as for other ICM processes, complex and expensive mould alignment systems are required, and the moulds are very expensive. In addition, since the clamp pressure causes closure of the mould and controlled movement of the core, the process can only be carried out on modified injection moulding machines, and in particular is not suitable to be carried out on all types of machines (for example, the process is not suited to direct lock machines).

A fourth injection compression moulding process is known as selective injection compression moulding (Select-ICM), or coining. The mould is completely closed and a separate core is pressed locally into the mould during or after injection of the material. This reduces the cavity volume and distributes the injected material throughout the mould cavity. However, coining is not known for use in the manufacture of containers. Coining is traditionally used for locally thinning an area of a moulding, such as a live hinge to improve its service life. This would only need a small hydraulic cylinder in the mould using a standard core-pulling valve on the machine. Compressing a minor area of a flat moulding to complete the fill is used but only where the product design will allow.

The viable commercial use of injection compression moulding processes for containers is in its infancy and has a long way to go before it is production viable and cost effective.

There is a need in the art for a cost effective, robust injection moulding process that at least partly overcomes the various problems with known processes as discussed above.

In particular, there is a need for an injection moulding process, and an apparatus therefor, that is suitable for producing containers, or preforms for containers, having high flow-length:wall thickness ratios, and/or low material stress, which can be produced using conventional injection moulding machines and therefore can be interfaced with the minimum of problems into conventional production practices.

The present invention aims at least partly to meet these needs in the art of container manufacture.

The present invention accordingly provides an injection mould for injection moulding an article having a base and a sidewall, the injection mould comprising: first and second mould parts which are adapted to be connected together in a fully closed configuration so as to define a mould cavity therebetween, in the fully closed configuration the first and second mould parts defining a cavity outer surface which defines the outer shape of the article to be moulded in the mould cavity, the mould cavity having a base-forming portion and a sidewall-forming portion for respectively forming a base and a sidewall of an article to be moulded, an injector for injecting into the mould cavity molten material to be moulded into the article, at least one portion of one of the first and second mould parts being movable when the first and second mould parts are in the fully closed configuration so as to vary the volume of the mould cavity in the fully closed configuration, an actuator for selectively moving the at least one portion of one of the first and second mould parts in first and second directions so as to increase and reduce, respectively, the volume of the mould cavity in the fully closed configuration.

The present invention further provides a method of injection moulding an article having a base and a sidewall, the method including the steps of: (a) providing an injection mould comprising first and second mould parts; (b) disposing the first and second mould parts in a fully closed configuration so as to define a mould cavity therebetween, in the fully closed configuration the first and second mould parts defining a cavity outer surface which defines the outer shape of the article to be moulded in the mould cavity, the mould cavity having a base-forming portion and a sidewall-forming portion for respectively forming a base and a sidewall of an article to be moulded; (c) injecting molten material into the cavity at an injection inlet of the cavity; and (d) moving at least one portion of one of the first and second mould parts away from the injection inlet during the injection thereby to vary the volume of the mould cavity in the fully closed configuration.

The present invention yet further provides an injection moulding apparatus for injection moulding a container or a preform for blow moulding into a container, the injection mould comprising: a plurality of mould parts which are adapted to be connected together in a fully closed configuration so as to define a mould cavity therebetween, in the fully closed configuration the plurality of mould parts defining a cavity outer surface which defines the outer shape of the article to be moulded in the mould cavity, the mould cavity having a base-forming portion and a sidewall-forming portion for respectively forming a base and a sidewall of the container or preform to be moulded, an injector for injecting into the mould cavity molten material to be moulded, an actuator for selectively moving one of the mould parts in the fully closed configuration thereby to vary a volume of the mould cavity adjacent to the injector in the fully closed configuration, and a control mechanism for controlling the direction of movement of the actuator thereby to vary a volume of the mould cavity adjacent to the injector in the fully closed configuration.

The present invention still further provides an injection mould for injection moulding an article having a base and a sidewall, the injection mould comprising: first and second mould parts which are adapted to be connected together in a fully closed configuration so as to define a mould cavity therebetween, in the fully closed configuration the first and second mould parts defining a cavity outer surface which defines the outer shape of the article to be moulded in the mould cavity, the mould cavity having a base-forming portion and a sidewall-forming portion for respectively forming a base and a sidewall of an article to be moulded, an injector for injecting into the mould cavity molten material to be moulded into the article, at least one portion of one of the first and second mould parts being movable when the first and second mould parts are in the fully closed configuration so as to vary the volume of the mould cavity in the fully closed configuration, and an actuator for selectively moving the at least one portion of one of the first and second mould parts in first and second directions so as to increase and reduce, respectively, the volume of the mould cavity in the fully closed configuration, the actuator including a moving part coupled to the at least one portion of one of the first and second mould parts, the moving part being commonly movable in the direction of movement of the at least one portion of one of the first and second mould parts.

This invention employs a mould in an injection moulding machine in which the filling pressure of the injected material to be moulded is controlled by moving the core, or a part of the core, away from the injection gate. Alternatively, it is possible to move the cavity, or part the cavity, in the same way. In either case, this movement of a mould part can vary the volume of the base portion of the mould cavity, and increase the base thickness opposite the gate, or close to the gate, and thereby reduce the filling pressure of the injected material.

Embodiments of the present invention will now be described by way of example only with reference to the accompanying drawings, in which.

Figure 1:
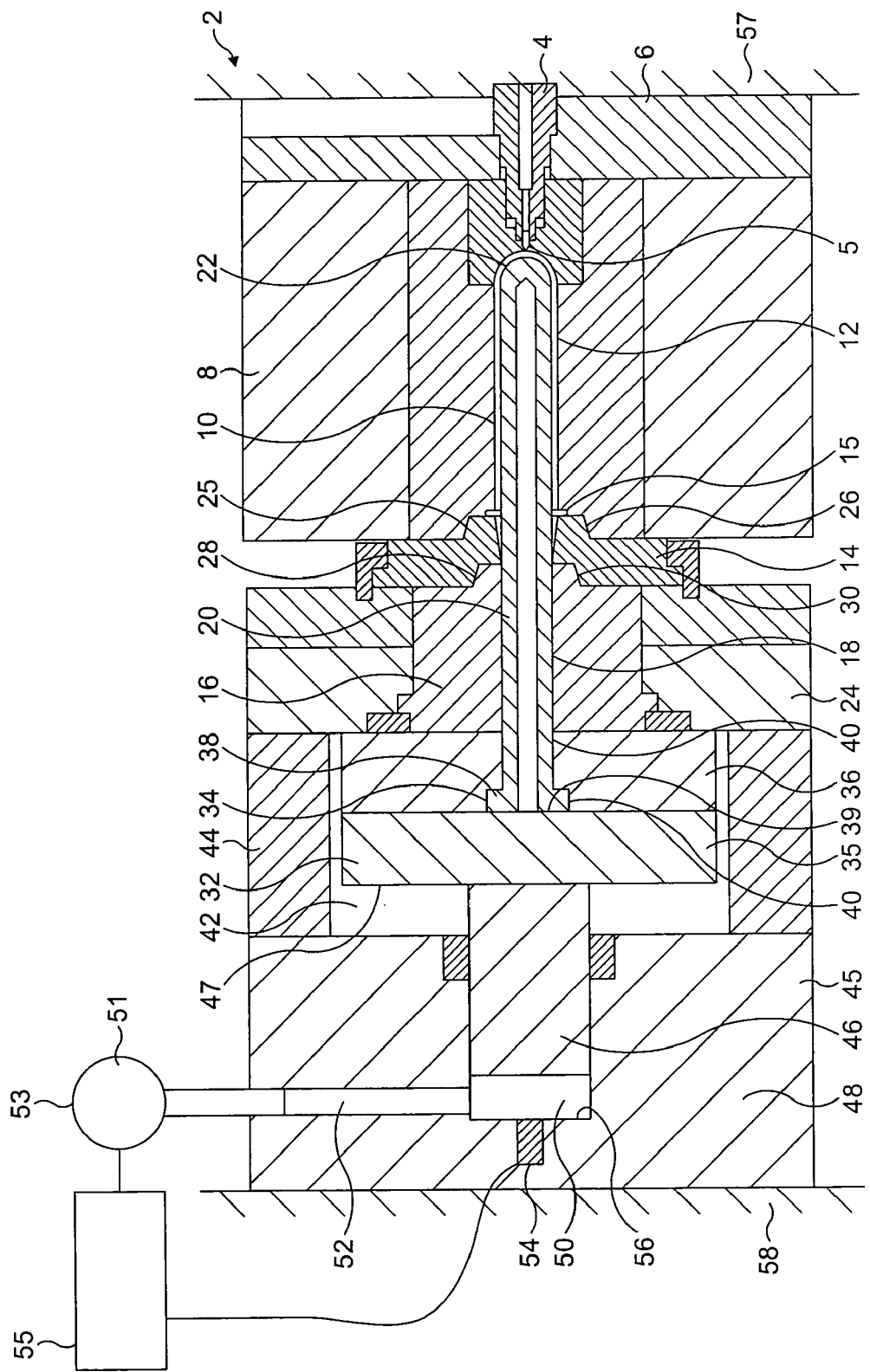
FIG. 1 is a schematic cross-section through an injection mould having a movable core in accordance with a first embodiment of the present invention.

Referring to FIG. 1, there is shown an injection mould (2) in accordance with a first embodiment of the present invention for injection moulding a preform, for example from polyester, particularly polyethylene terephthalate (PET), for subsequent blow moulding to form a container. The injected material to be moulded is injected through a feed nozzle (4) in a first back plate (6) of the injection mould (2). A cavity plate (8) is adjacent to the first back plate (6) and defines an injection mould cavity (10). A gate (5) of the feed nozzle (4) opens into the cavity (10). The cavity plate (8) forms an outer surface (12) of the cavity (10) which in use defines the outer shape of the article to be injection moulded. A plurality of neck splits (14) is provided at the end (15) of the cavity (10) remote from the feed nozzle (4). The neck splits (14) are shaped to mould the outer shape of one end of the article to be injection moulded (in this embodiment the neck finish of a preform for subsequent blow moulding to form a bottle). The neck splits (14) also support the injection moulded article as it is removed from the cavity (10) after the injection moulded material has solidified.

A core bearing (16) is adjacent to the plurality of neck splits (14) and has a central bore (18) in which an elongate core (20) is slidably received. The elongate core (20) can be translated in a longitudinal direction coaxial with the axis of the cavity (10) and with the feed nozzle (4). Accordingly, the core (20) can selectively be slid in the core bearing (16) forwardly in a direction into the cavity (10) towards the feed nozzle (4) or rearwardly in a direction out of the cavity (10) away from the feed nozzle (4). Such forward and backward movement can vary the distance of the free end (22) of the core (20) from the feed nozzle (4). The core bearing (16) is received within an annular core bearing support (24).

The neck splits (14) have a tapering male portion (25) (which is typically frustoconical) which is fitted into a complementary tapering female portion (26) in the cavity plate (8). Correspondingly, the core bearing (16) has a tapering male portion (28) (which is typically frustoconical) which is fitted into a complementary tapering female portion (30) in the neck splits (14). Thereby the core (20) and the neck splits (14) are axially centered with respect to the axis of the cavity (10).

A pressure plate assembly (32) is fitted to the end (34) of the core (20) remote from the free end (22) that is within the cavity (10). The pressure plate assembly (32) is axially fixed relative to the core (20) so that longitudinal movement of the pressure plate assembly (32) correspondingly causes longitudinal movement of the core (20) within the cavity (10). The pressure plate assembly (32) comprises a pair of adjacent plate members (35, 36) between which the end (34) of the core (20) is locked. The end (34) of the core (20) includes an annular flange (38) that is radially outwardly directed relative to the cylindrical outer surface (40) of the remainder of the core (20). A planar end plate member (35) of the pressure plate assembly (32) is disposed against the transverse end surface (39) of the flange (38) and an intermediate plate member (36) of the pressure plate assembly (32) has a central hole (40) therein in which the end (34) of the core (20), including the flange (38), is snugly received, so that the flange (38), and thereby the core (20), is captive in the pressure plate assembly (32). The pressure plate assembly (32) is disposed within a chamber (42) defined by an annular housing (44) adjacent to the core bearing support (24).

A hydraulic piston and cylinder assembly (45) is mounted adjacent to the housing (44). The piston (46) in the hydraulic piston and cylinder assembly (45) is mounted for translational forward and backward longitudinal movement along a direction coaxial with the axis of the core (20), and bears against an end face (47) of the pressure plate assembly (32). The cylinder (48) of the hydraulic piston and cylinder assembly (45) includes a hydraulic chamber (50) having a fluid inlet (52) for connection to a source of pressurised hydraulic fluid (51) including a hydraulic pressure device (53).

A transducer (54) is mounted in a wall (56) of the hydraulic chamber (50) and can measure the pressure of the hydraulic fluid in the hydraulic chamber (50).

Accordingly, the hydraulic fluid in the hydraulic chamber (50) can be pressurised by the hydraulic pressure device (53) and thereby cause the hydraulic piston (46) to be urged in a direction out of the hydraulic chamber (50). This in turn urges the core (20), via the pressure plate assembly (32), forwardly in a direction into the cavity (10) towards the feed nozzle (4), subject to the forward pressure applied to the core (20) overcoming any reverse injection pressure in the cavity (10). Conversely, when the injection pressure in the cavity (10) applies a rearward force on the core (20) that is greater than the forward force on the core (20) as a result of the applied hydraulic pressure on the pressure plate assembly (32), the core (20) is urged rearwardly in a direction out of the cavity (10) away from the feed nozzle (4).

The transducer (54) is employed continuously, or periodically, to measure the pressure of the hydraulic fluid in the hydraulic chamber (50), and such measurement can be employed to provide a dynamic control of the hydraulic pressure, and thereby the movement and position of both the piston (46) and the core (20). In this way, the position of the core (20) relative to the cavity (10) is dynamically controlled in order to maintain a specific pressure condition within the injection mould cavity (10) during the injection moulding process.

The transducer (54) is electrically connected to a controller (55) for the hydraulic pressure device (53). The controller (55) may comprises a processor that is preprogrammed selectively to operate the hydraulic pressure device (53) so as to maintain throughout an injection moulding cycle a predetermined hydraulic pressure in the hydraulic chamber (50), and to vary the hydraulic pressure with time within the injection moulding cycle so as to provide, at any particular phase or time within the cycle, a particular hydraulic pressure, and thereby a particular longitudinal position for the core (20) along its axis within the cavity (10).

When the core (20) is moved forward against the injected material, the melt pressure maintained by the injection system (not shown) supplying molten plastics material to the feed nozzle (4) is increased to balance the increasing pressure within the mould cavity (10). This causes either more material to be injected into the cavity (10) to help completely fill the mould cavity (10), or some of the material to move back though the gate (5) and the feed nozzle (4) if the cavity pressure is higher than the injection pressure within the feed nozzle (4).

In use, the injection mould (2) is kept in a closed configuration—the back plate (6) and the hydraulic cylinder (48) of the hydraulic piston and cylinder assembly (45) are disposed between two platens (57, 58) of an injection moulding machine. The platens (57, 58) are urged together throughout the entire injection moulding process. This retains the core bearing (16), neck splits (14) and cavity plate (8) engaged together until the injected material has solidified sufficiently within the cavity (10) to permit the injection moulded article safely to be ejected therefrom. This is achieved by opening up of the cavity (10) and removal of the injection moulded article supported on the neck splits (14), without any subsequent significant, e.g. greater than about 5%, change in shape or dimensions (for example post-moulding shrinkage).

Figure 2:
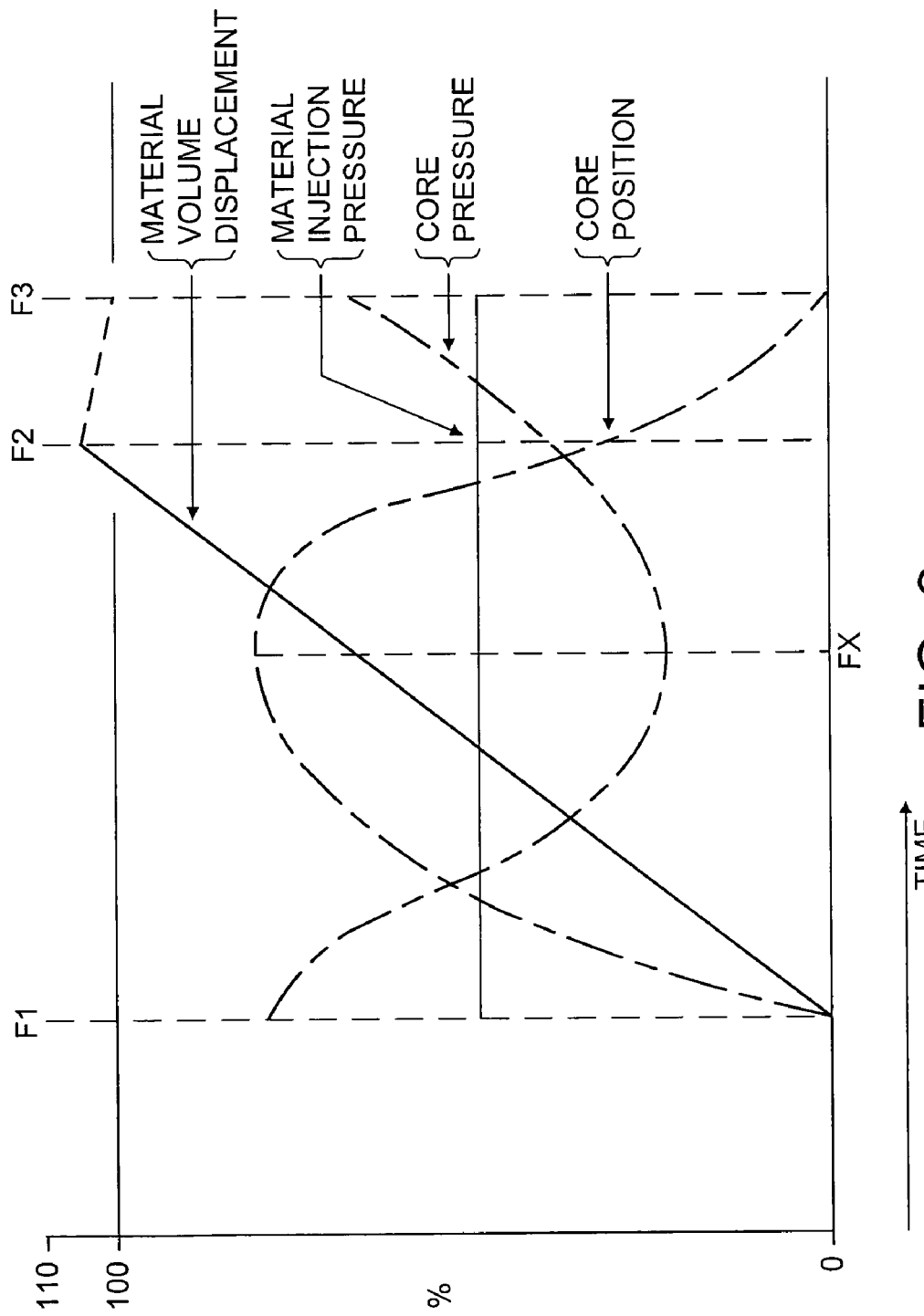
FIG. 2 is a graph showing schematically the operation of the injection mould of FIG. 1.

FIG. 2 is a graph showing schematically the operation of the injection mould of FIG. 1. The relationship with time of various mould parameters is shown over the course of a single injection moulding cycle. Throughout the entire injection moulding cycle the injection mould is fully closed, and the platens (57, 58) are urged together under a predetermined clamp pressure throughout the entire injection moulding process. However, the core (20) is permitted to move under dynamic control to vary the volume of the cavity (10).

At time F1 the injection moulding cycle is started.

In a first phase, the material is injected through the gate (4) at a constant volumetric rate, represented by the linearly increasing material volume displacement shown in FIG. 2. In the gate (4), the material is maintained at a constant machine injection pressure, represented by the linearly horizontal machine injection pressure. As the material is injected through the gate (4), a pressure acting on the free end (22) of the core, identified as the core pressure in FIG. 2, is established. This core pressure is detected by the transducer (54) via the hydraulic piston and cylinder assembly (45). The transducer (54) then acts to output a pressure signal that is used by controller (55) to control the operation of the hydraulic piston and cylinder assembly (45), and thereby the position of the core (20), and consequently the pressure acting on the free core (20) 'in the region between the core (20) and the gate (4). Substantially immediately after time F1, the core (20) is moved rearwardly away from the gate (4), and the core position is shown in FIG. 2 (the 0% value at the origin represents the core being fully forward and the 100% value on the ordinate represents the core being fully rearward). Correspondingly, the core pressure falls as the core (20) is moved rearwardly away from the gate (4), since the rearward movement of the core (20) tends to lower the core pressure.

In the illustrated embodiment, the first phase terminates at a time FX, when the cavity is only partly filled with the injected material, and typically the cavity is at least about 70% full, the core pressure reaches its minimum values and the core (20) is positioned at its most rearward location away from the gate (4). It is to be noted that the core only needs to move back enough to maintain the cavity pressure, and it may never reach its rearward mechanical limit. Typically, core is moved away from the gate so as to vary the separation distance therebetween, at a region of the mould cavity in the vicinity of the injector, by a factor of at least two times the width of the separation distance when the mould cavity has its minimum volume. More preferably, for a preform the separation distance is varied by a factor of from 5 to 15, most preferably 10, times the width of the separation distance when the mould cavity has its minimum volume. Then, in a second phase, as the material continues to be injected through the gate (4) at the same constant volumetric rate, the core pressure is increased and the core (20) is moved forwardly towards the gate (4). At a time F2 the injection of material into the cavity, and the second phase, are terminated. At this time, the cavity has been overfilled with the injected material as compared to the 100% amount required to form the desired preform. Typically, the overfill is from 2 to 10%, more typically about 5% At time F2 the core (20) is still displaced rearwardly from its final moulding position, but at an intermediate position as compared to that at time FX.

Thereafter, in final third phase within a period from time F2 to time F3 at the end of the injection moulding cycle, the core (20) continues to be displaced forwardly towards its final moulding position and the core pressure continues correspondingly to increase, during which time the machine injection pressure is still maintained constant. Such continued movement of the core (20) when the cavity is overfilled causes the injected material to be packed in the cavity (10) at the machine injection pressure and also causes excess material to be pushed back through the gate (4). At time F3 the cavity is 100% filled, and the core (20) is back at its initial position.

It may be seen from FIG. 2 that the core pressure is controlled so that for a substantial period of the injection moulding cycle the core pressure is less than the machine injection pressure. This means that in the resultant injection moulded preform there is a low residual stress resulting from the injection moulding process. Also, there is no need for a separate packing cycle after the core has stopped moving. The last phase of the injection moulding cycle between F2 and F3, in which the cavity overfill is eliminated, causes the required packing of the material as the core moves back to its final position. By providing a cavity overfill that is eliminated at the end of the injection moulding cycle, this obviates the need for a predetermined metered dose of material to be injected, and consequently avoids the requirement for metering systems, or "shooting pots" to be provided in the injection moulding apparatus. The required amount of material to be present in the final preform is controlled by movement of the core, which in turn is controlled by a pressure signal from the transducer.

In FIG. 2, the various parameters are only shown qualitatively by way of example, as they would vary from mould to mould and dependent upon the particular articles being produced, as well as on the material, structural and process parameters. However, the general principles illustrated between the core pressure and the machine injection pressure, and the core position as well as the material volume displacement, apply generally in the method of the present invention.

It would be readily apparent to the skilled person knowledgeable of injection moulding methods and apparatus how to apply these general principles to a specific mould configuration to manufacture a specific injection moulded article using the methods and injection moulds of the present invention disclosed herein.

In alternative embodiments, in the first phase the cavity may be fully filled or even overfilled, so that the filling range is typically from 70 to 105% in the first phase, and the first phase terminates at a time FX which may correspond even as late as up to time F2 at which the when there is overfilling and the filling by injecting material through the gate (4) is terminated—in other words the second phase may be omitted, and the first filling phase may achieve overfilling directly which is immediately followed by the third phase at which the cavity is overfilled and the core is returned to its original position by forward motion.

Also, in the illustrated embodiment a single detector in the form of pressure transducer is employed. In alternative embodiments, several detectors can be used and either one used to control pressure and the other used to monitor pressure, or all of the detectors can be used to control and monitor pressure, and the controller is used to calculate the mean pressure from the various detectors.

Figure 3:
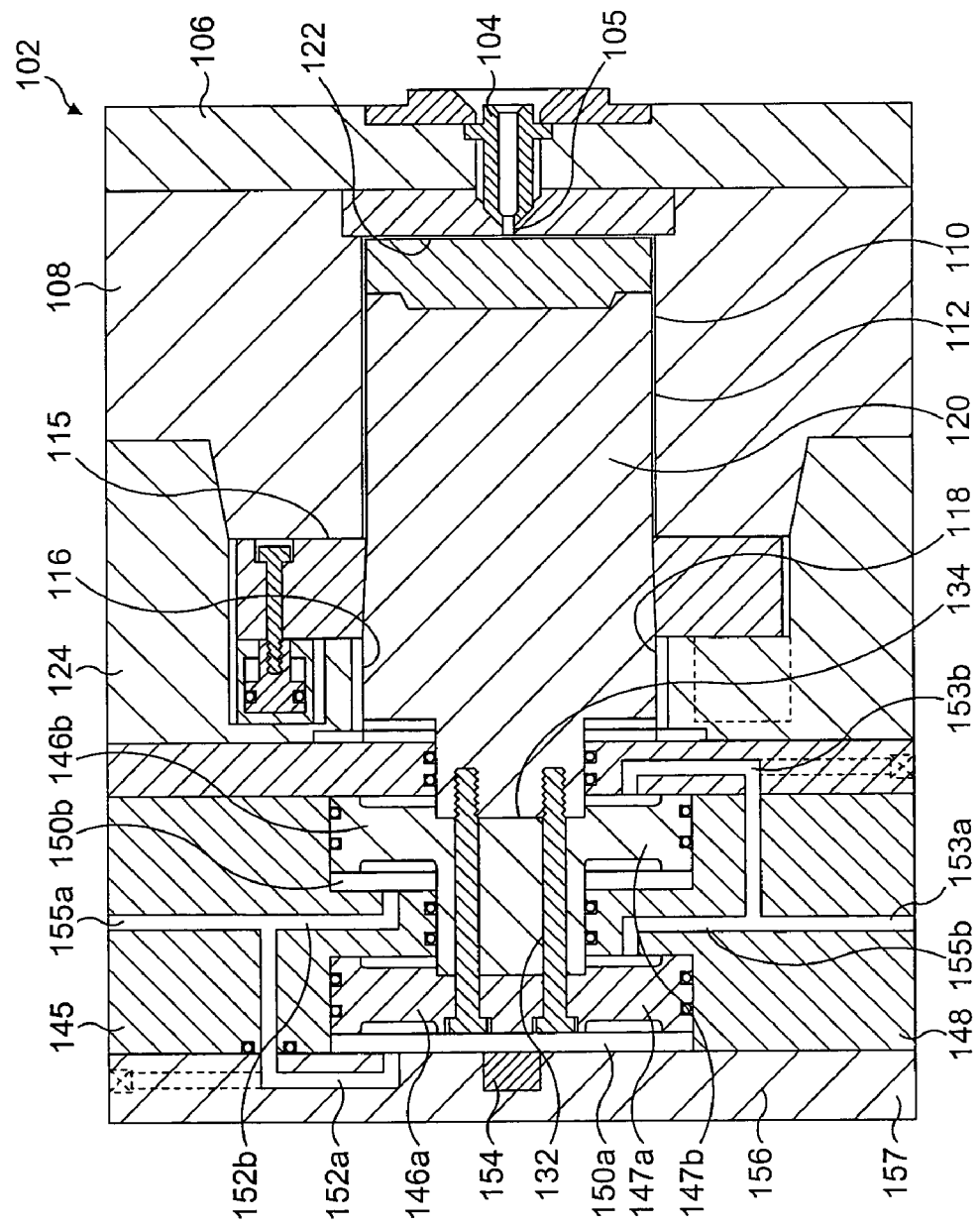
FIG. 3 is a schematic cross-section through an injection mould having a movable core in accordance with a second embodiment of the present invention.

FIG. 3 is a schematic cross-section through an injection mould having a movable core in accordance with a second embodiment of the present invention in which the injection mould (102) is for injection moulding a cylindrical container, for example a paint, can, for example from a polyolefin, particularly polypropylene (PP) or polyethylene (PE).

As for the first embodiment, the injected material to be moulded is injected through a feed nozzle (104) in a first back plate (106) of the injection mould (102). A cavity plate (108) is adjacent to the first back plate (106) and defines an injection mould cavity (110). A gate (105) of the feed nozzle (104) opens into the cavity (110). The cavity plate (108) forms an outer surface (112) of the cavity (110) which in use defines the outer shape of the article to be injection moulded.

A pneumatic stripper ring (115) and an adjacent core bearing (116) are, in turn, adjacent to the cavity plate (108). The core bearing (116) has a central bore (118) in which an elongate core (120) is slidably received. The elongate core (120) can be translated in a longitudinal direction coaxial with the axis of the cavity (110) and with the feed nozzle (104) to vary the distance of the free end (122) of the core (120) from the feed nozzle (104). The core bearing (116) is received within an annular core bearing support (124). The pneumatic stripper ring (115), in known manner, can be actuated to urge the moulded container off the core (120) after the mould has started to open.

A hydraulic piston and cylinder assembly (145) is mounted adjacent to the core bearing support (124). Two longitudinally spaced pistons (146a, 146b) are fitted to the end (134) of the core (120) remote from the free end (122) that is within the cavity (110). The pistons (146a, 146b) are axially fixed relative to the core (120), for example by bolts, so that longitudinal movement of the pressure pistons (146a, 146b) correspondingly causes longitudinal movement of the core (120) within the cavity (110). The two longitudinally spaced pistons (146a, 146b) in the hydraulic piston and cylinder assembly (145) are mounted for translational forward and backward longitudinal movement along a direction coaxial with the axis of the core (120). Each piston (146a, 146b) includes an outer annular part (147a, 147b) that is received within a respective hydraulic chamber (150a, 150b) of a cylinder part (148) of the hydraulic piston and cylinder assembly (145). Each hydraulic chamber (150a, 150b) has a first fluid inlet (152a, 152b) on one side of the respective piston (146a, 146b) and a second fluid inlet (153a, 153b) on the other side of the respective piston (146a, 146b) for respective connection, via a respective first or second common conduit (155a, 155b) to a source of pressurised hydraulic fluid (not shown) including a hydraulic pressure device (not shown).

A transducer (154) is mounted in a wall (156) of the rearmost hydraulic chamber (150a) being part of a second back plate (157) and can measure the pressure of the hydraulic fluid in the hydraulic chamber (150a).

Accordingly, similar to the first embodiment, the hydraulic fluid in the hydraulic chambers (150a, 150b) can be pressurised by the hydraulic pressure device, and a pressure differential between the first and second fluid inlets (152a, 152b) can be established and thereby cause the hydraulic pistons (146a, 146b) commonly selectively to be urged in a forward direction along the respective hydraulic chamber (150a, 150b). This in turn urges the core (120), forwardly in a direction into the cavity (110) towards the feed nozzle (104). Conversely, when the pressure differential between the first and second fluid inlets (152a, 152b) and/or the injection pressure in the cavity (110) applies a rearward force on the core (120) that is greater than the forward force on the core (120) as a result of the applied hydraulic pressure on the hydraulic pistons (146a, 146b), the core (120) is urged rearwardly in a direction out of the cavity (110) away from the feed nozzle (104).

As for the first embodiment, the transducer (154) is employed continuously, or periodically, to measure the pressure of the hydraulic fluid in the hydraulic chamber (150a), and such measurement can be employed to provide a dynamic control of the hydraulic pressure, and thereby the movement and position of the core (120). In this way, the position of the core (120) relative to the cavity (110) is dynamically controlled in order to maintain a specific pressure condition within the injection mould cavity (110) during the injection moulding process.

In this embodiment for making a container having a thin walled base, which may be as thin as 0.3 mm, typically core is moved away from the gate so as to vary the separation distance therebetween, at a region of the mould cavity in the vicinity of the injector, by a factor of at least two times the width of the separation distance when the mould cavity has its minimum volume. More preferably, for a container the separation distance is varied by a factor of from 2 to 10 times the width of the separation distance when the mould cavity has its minimum volume.

In this embodiment, the provision of plural longitudinally spaced pistons (146a, 146b) provides a specific technical advantage—the force applied by the hydraulic piston and cylinder assembly, as actuator for the core, on the core can be increased without increasing the diameter of the actuator. This reduces the radial dimensions of the actuator, and therefore the mould. Furthermore, the additional length of the actuator can increase the radial stiffness of the actuator and the corresponding moving mould parts, partly as a result of increased bearing length, which tends to reduce any inadvertent radial deflection of the core. As discussed herein, core deflection is a problem with known moulds, and the present invention provides not only a mould construction which inherently provides improved mould centering, since the core is moved only when the mould is fully closed, but also a mould construction where the core actuator has high inherent stiffness, further reducing potential problems associated with non-centering of the core during the injection moulding process.

In addition, in accordance with the present invention generally, the actuator for moving the movable mould part (i.e. core, core pad, or cavity wall) when the core is closed is disposed in the mould and can be aligned longitudinally with respect to the direction of movement. This can permit the bearing length for the moving part to be higher than in known moulds, for example the core bearing length being at least 3 times, more preferably at least 5 times, the diameter of the core, which in turn can provide a very high radial stiffness for the core which would tend to reduce any inadvertent non-centering of the core during the injection moulding process.

Figure 4:
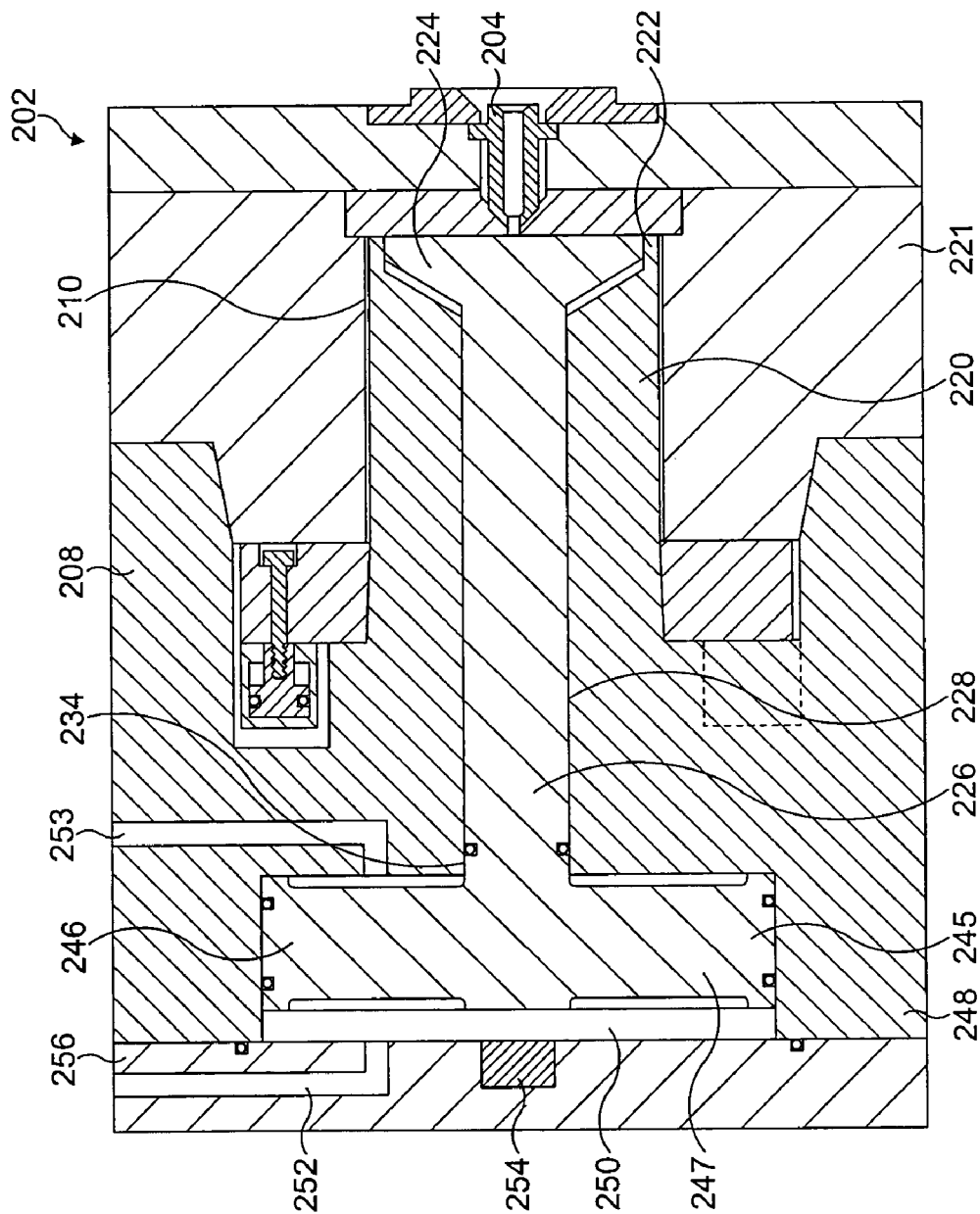
FIG. 4 is a schematic cross-section through an injection mould having a movable core part in accordance with a third embodiment of the present invention.

FIG. 4 is a schematic cross-section through an injection mould having a movable core part in accordance with a third embodiment of the present invention in which the injection mould (202) is for injection moulding a cylindrical container, for example a paint can, for example from a polyolefin, particularly polypropylene (PP) or polyethylene (PE).

The injection mould (202) is modified as compared to the second embodiment in two primary respects.

First, the majority of the core (220) is fixed, being integral with a core plate (208), and only a central part, in the form of a pad (224), of the free end (222) of the core (220) opposite to the feed nozzle (204) is longitudinally movable to vary the size of the injection mould cavity (210) defined between the core (220) and the cavity plate (221). The pad (224) has a longitudinal extension (226) that extends through a central bore (228) of the core (220) rearwardly towards the hydraulic piston and cylinder assembly (245).

Second, a single piston (246) of the hydraulic piston and cylinder assembly (245) is fitted to the rearward end (234) of the longitudinal extension (226). The piston (246) is axially fixed relative to the longitudinal extension (226), for example by being integral therewith, so that longitudinal movement of the piston (246) correspondingly causes longitudinal movement of the pad (224) within the cavity (210). The piston (246) includes an outer annular part (247) that is received within a hydraulic chamber (250) of a cylinder part (248) of the hydraulic piston and cylinder assembly (245). The hydraulic chamber (250) has a first fluid inlet (252) on one side of the piston (246) and a second fluid inlet (253) on the other side of the piston (246) for respective connection to a source of pressurised hydraulic fluid (not shown) including a hydraulic pressure device (not shown).

A transducer (254) is mounted in a wall (256) of the hydraulic chamber (250) and can measure the pressure of the hydraulic fluid in the hydraulic chamber (250).

Accordingly, similar to the first and second embodiments, the hydraulic fluid in the hydraulic chamber (250) can be pressurised by the hydraulic pressure device, and thereby cause the hydraulic piston (246) selectively to be urged in a forward direction along the hydraulic chamber (250). This in turn urges the pad (224) of the core (220) forwardly in a direction into the cavity (210) towards the feed nozzle (204). Conversely, when the pressure differential between the first and second fluid inlets (252, 253) and/or the injection pressure in the cavity (210) applies a rearward force on the pad (224) of the core (220) that is greater than the forward force on the pad (224) of the core (220) as a result of the applied hydraulic pressure on the hydraulic piston (246), the pad (224) of core (220) is urged rearwardly in a direction out of the cavity (210) away from the feed nozzle (204).

As for the first and second embodiments, the transducer (254) is employed continuously, or periodically, to measure the pressure of the hydraulic fluid in the hydraulic chamber (250), and such measurement can be employed to provide a dynamic control of the hydraulic pressure, and thereby the movement and position of the pad (224) of the core (220). In this way, the position of the pad (224) of the core (220) relative to the cavity (210) is dynamically controlled in order to maintain a specific pressure condition within the injection mould cavity (210) during the injection moulding process.

Figure 5:
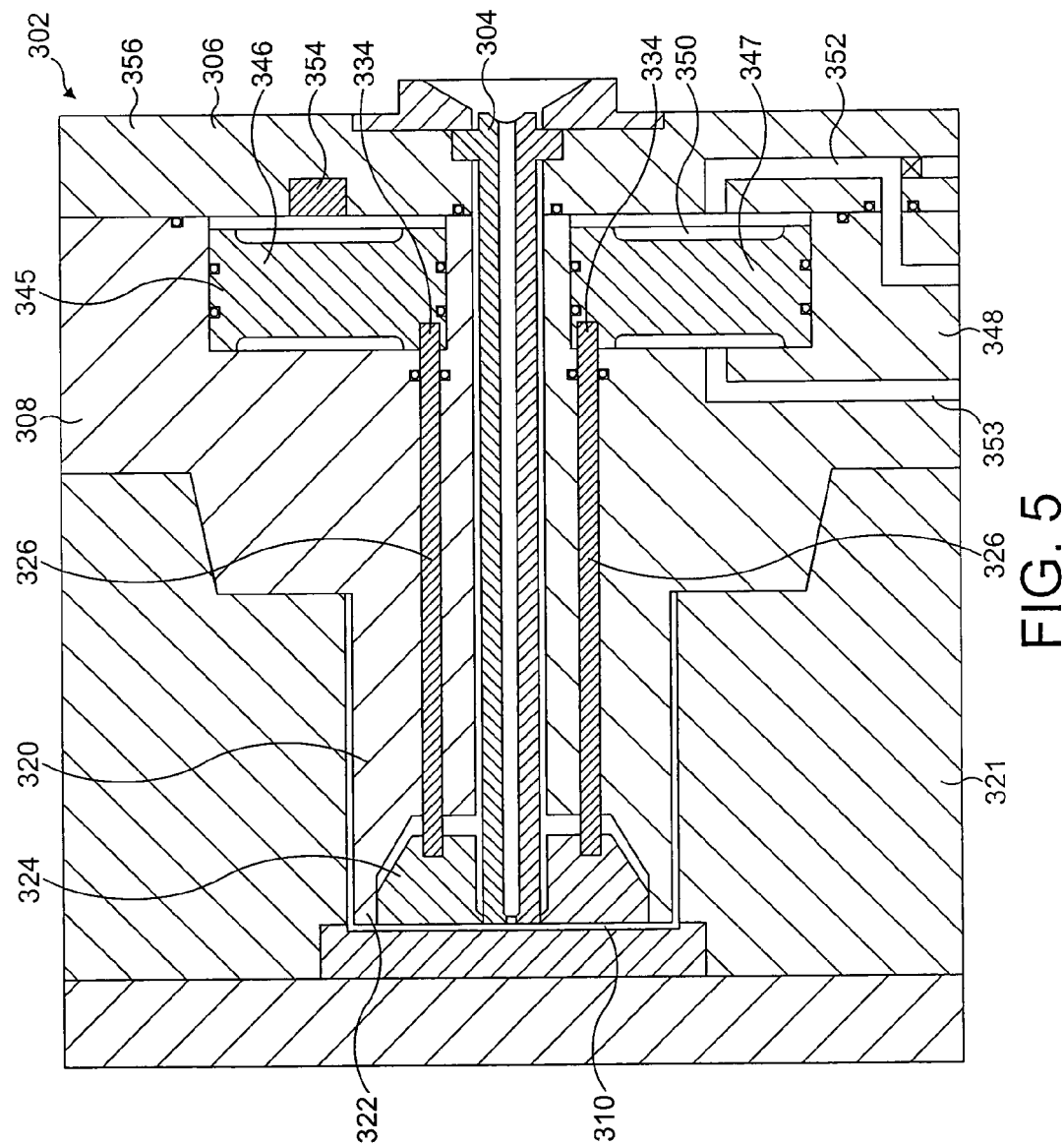
FIG. 5 is a schematic cross-section through an injection mould having a movable core part in accordance with a fourth embodiment of the present invention.

FIG. 5 is a schematic cross-section through an injection mould having a movable core part in accordance with a fourth embodiment of the present invention in which the injection mould (302) is for injection moulding a cylindrical container, for example a paint can, for example from a polyolefin, particularly polypropylene (PP) or polyethylene (PE).

The injection mould (302) is modified as compared to the third embodiment by providing a feed nozzle within the core, and within the movable core pad, so that the injection mould (302) can be employed in an injection moulding process incorporating in-mould labeling (IML).

The majority of the core (320) is fixed, being integral with a core plate (308), and only a central part, in the form of a pad (324), of the free end (322) of the core (320) is longitudinally movable to vary the volume of the injection mould cavity (310). The pad (324) is mounted on a plurality of longitudinal arms (326) that extend in a slidable manner through the core (320) rearwardly towards the hydraulic piston and cylinder assembly (345).

A feed nozzle (304) extends through the back plate (306), through the core (320) and through to the pad (324). The pad (324) can slide along the feed nozzle (304). The feed nozzle (304) opens into the cavity (310) defined between the cavity plate (321) and the core (320).

A piston (346) of the hydraulic piston and cylinder assembly (345) is fitted to the rearward ends (334) of the longitudinal arms (326). The piston (346) is axially fixed relative to the longitudinal arms (326) so that longitudinal movement of the piston (346) correspondingly causes longitudinal movement of the pad (324) within the cavity (310). The piston (346) is an annular body (347) that is received within an annular hydraulic chamber (350) of a cylinder part (348) of the hydraulic piston and cylinder assembly (345). The hydraulic chamber (350) has a first fluid inlet (352) on one side of the piston (346) and a second fluid inlet (353) on the other side of the piston (346) for respective connection to a source of pressurised hydraulic fluid (not shown) including a hydraulic pressure device (not shown).

A transducer (354) is mounted in a wall (356) of the hydraulic chamber (350) and can measure the pressure of the hydraulic fluid in the hydraulic chamber (350).

Accordingly, similar to the first, second and third embodiments, the hydraulic fluid in the hydraulic chamber (350) can be pressurised by the hydraulic pressure device, and thereby cause the hydraulic piston (346) selectively to be urged in a forward direction along the hydraulic chamber (350). This in turn urges the pad (324) of the core (320) forwardly in a direction into the cavity (310). Conversely, when a pressure differential between the first and second fluid inlets (352, 353) and/or the injection pressure in the cavity (310) applies a rearward force on the pad (324) of the core (320) that is greater than the forward force on the pad (324) of the core (320) as a result of the applied hydraulic pressure on the hydraulic piston (346), the pad (324) of core (320) is urged rearwardly in a direction out of the cavity (310).

As for the previous embodiments, the transducer (354) is employed continuously, or periodically, to measure the pressure of the hydraulic fluid in the hydraulic chamber (350), and such measurement can be employed to provide a dynamic control of the hydraulic pressure, and thereby the movement and position of the pad (324) of the core (320). In this way, the position of the pad (324) of the core (320) relative to the cavity (310) is dynamically controlled in order to maintain a specific pressure condition within the injection mould cavity (310) during the injection moulding process.

Figure 6:
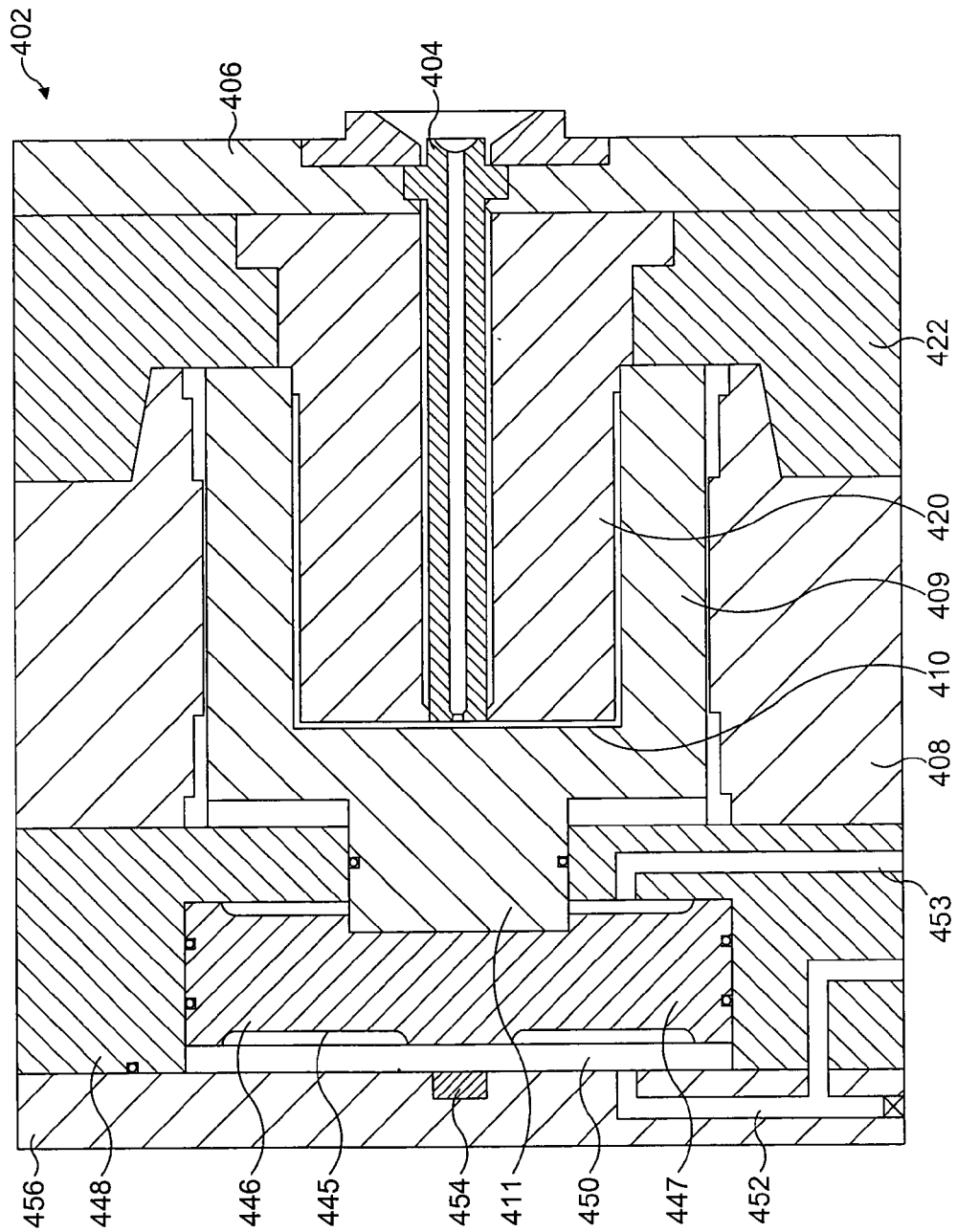
FIG. 6 is a schematic cross-section through an injection mould having a movable cavity part in accordance with a fifth embodiment of the present invention.

FIG. 6 is a schematic cross-section through an injection mould having a movable cavity part in accordance with a fifth embodiment of the present invention in which the injection mould (402) is for injection moulding a cylindrical container, for example a paint can, for example from a polyolefin, particularly polypropylene (PP) or polyethylene (PE).

The injection mould (402) is modified as compared to the fourth embodiment by providing a fixed core, and a movable cavity plate. In other words, instead of providing a movable core or pad together with a fixed cavity as in the previous embodiments, the core is fixed and the cavity is movable.

The core (420) is fixed, being mated with or integral with a core plate (422), and a feed nozzle (404) extends through the back plate (406) and through the core (420). The feed nozzle (404) opens into the cavity (410).

A movable cavity part (409) surrounds the core (420) and is longitudinally movable to vary the size of the injection mould cavity (410). The movable cavity part (409) is slidably mounted within a fixed cavity plate (408).

An extension (411) of the movable cavity part (409) is connected to a piston (446) of a hydraulic piston and cylinder assembly (445).

The piston (446) is axially fixed relative to the movable cavity part (409) so that longitudinal movement of the piston (446) correspondingly causes longitudinal movement of the movable cavity part (409) thereby to vary the volume of the cavity (410). The piston (446) includes an outer annular part (447) that is received within a hydraulic chamber (450) of a cylinder part (448) of the hydraulic piston and cylinder assembly (445). The hydraulic chamber (450) has a first fluid inlet (452) on one side of the piston (446) and a second fluid inlet (453) on the other side of the piston (446) for respective connection to a source of pressurised hydraulic fluid (not shown) including a hydraulic pressure device (not shown).

A transducer (454) is mounted in a wall (456) of the hydraulic chamber (450) and can measure the pressure of the hydraulic fluid in the hydraulic chamber (450).

Accordingly, similar to the previous embodiments, the hydraulic fluid in the hydraulic chamber (450) can be pressurised by the hydraulic pressure device, and thereby cause the hydraulic piston (446) selectively to be urged in a forward or rearward direction along the hydraulic chamber (450) so as to vary the volume of the cavity (410) by corresponding movement of the movable cavity part (409).

As for the previous embodiments, the transducer (454) is employed continuously, or periodically, to measure the pressure of the hydraulic fluid in the hydraulic chamber (450), and such measurement can be employed to provide a dynamic control of the hydraulic pressure, and thereby the movement and position of the movable cavity part (409). In this way, the position of the movable cavity part (409), and thereby the volume of the cavity (410) is dynamically controlled in order to maintain a specific pressure condition within the injection mould cavity (410) during the injection moulding process.

Figure 7:
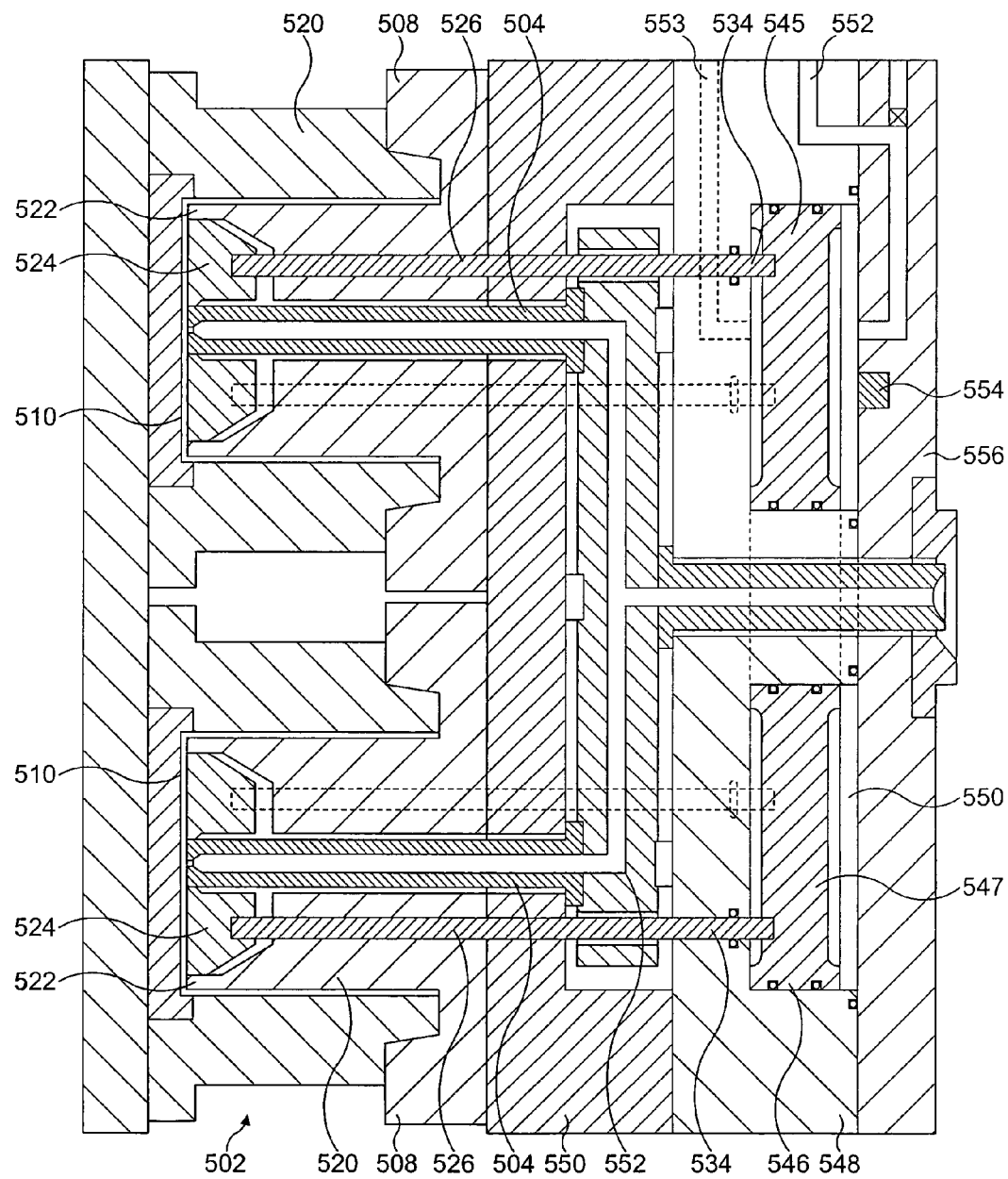
FIG. 7 is a schematic cross-section through a multiple cavity injection mould, each cavity having a movable core part in accordance with a sixth embodiment of the present invention.

FIG. 7 is a schematic cross-section through a multiple cavity injection mould, each cavity having a respective movable core part, in accordance with a sixth embodiment of the present invention in which the injection mould (502) is for simultaneous injection moulding a plurality of cylindrical containers, for example a paint can, for example from a polyolefin, particularly polypropylene (PP) or polyethylene (PE).

The injection mould (502) is similar to the fourth embodiment by providing a feed nozzle within the core, and within the movable core pad, so that the injection mould (502) can be employed in an injection moulding process incorporating in-mould labeling. Two (or more) mould cavities are provided that are connected to a common feed system and to a common hydraulic piston and cylinder assembly for moving the movable core pads.

In each mould cavity, the majority of the core (520) is fixed, being integral with a core plate (508), and only a central part, in the form of a pad (524), of the free end (522) of the core (520) is longitudinally movable to vary the size of the respective injection mould cavity (510). The pad (524) is mounted on at least one longitudinal arm (526) that extends in a slidable manner through the core (520) rearwardly towards the hydraulic piston and cylinder assembly (545).

In each mould cavity, a respective feed nozzle (504) extends, from a common manifold plate (550), through the core (520) and through to the pad (524). The pad (524) can slide along the feed nozzle (504). The feed nozzle (504) opens into the cavity (510). A common hot runner system (552) connects to the feed nozzles (504) within the common manifold plate (550).

A common annular piston (546) of the hydraulic piston and cylinder assembly (545) is fitted to the rearward ends (534) of the longitudinal arms (526). The piston (546) is axially fixed relative to the longitudinal arms (526) so that longitudinal movement of the piston (546) correspondingly causes longitudinal movement of both of the pads (524) within the respective cavities (510). The piston (546) is an annular body (547) that is received within an annular hydraulic chamber (550) of a cylinder part (548) of the hydraulic piston and cylinder assembly (545). The hydraulic chamber (550) has a first fluid inlet (552) on one side of the piston (546) and a second fluid inlet (553) on the other side of the piston (546) for respective connection to a source of pressurised hydraulic fluid (not shown) including a hydraulic pressure device (not shown).

A transducer (554) is mounted in a wall (556) of the hydraulic chamber (550) and can measure the pressure of the hydraulic fluid in the hydraulic chamber (550).

Accordingly, similar to the previous embodiments, the hydraulic fluid in the hydraulic chamber (550) can be pressurised by the hydraulic pressure device, and thereby cause the hydraulic piston (546) selectively to be urged in a forward direction along the hydraulic chamber (550). This in turn urges the plurality of pads (524) of the respective cores (520) forwardly in a direction into the respective cavity (510). Conversely, when a pressure differential between the first and second fluid inlets (552, 553) and/or the injection pressure in the cavities (510) applies a rearward force on the pads (524) of the cores (520) that is greater than the forward force on the pads (524) of the cores (520) as a result of the applied hydraulic pressure on the hydraulic piston (546), the pads (524) of cores (520) are urged rearwardly in a direction out of the respective cavity (510).

As for the previous embodiments, the transducer (554) is employed continuously, or periodically, to measure the pressure of the hydraulic fluid in the hydraulic chamber (550), and such measurement can be employed to provide a dynamic control of the hydraulic pressure, and thereby the movement and position of the pads (524) of the cores (520). In this way, the position of the pads (524) of the cores (520) relative to the cavity (310) is commonly dynamically controlled in order to maintain a specific pressure condition within the injection mould cavities (510) during the injection moulding process. For the multiple cavity injection mould, not only is a common hot runner system provided, but also a common hydraulic system for controlling the cavity volume and the cavity pressure is provided for the multiple cavities.

Figure 8:
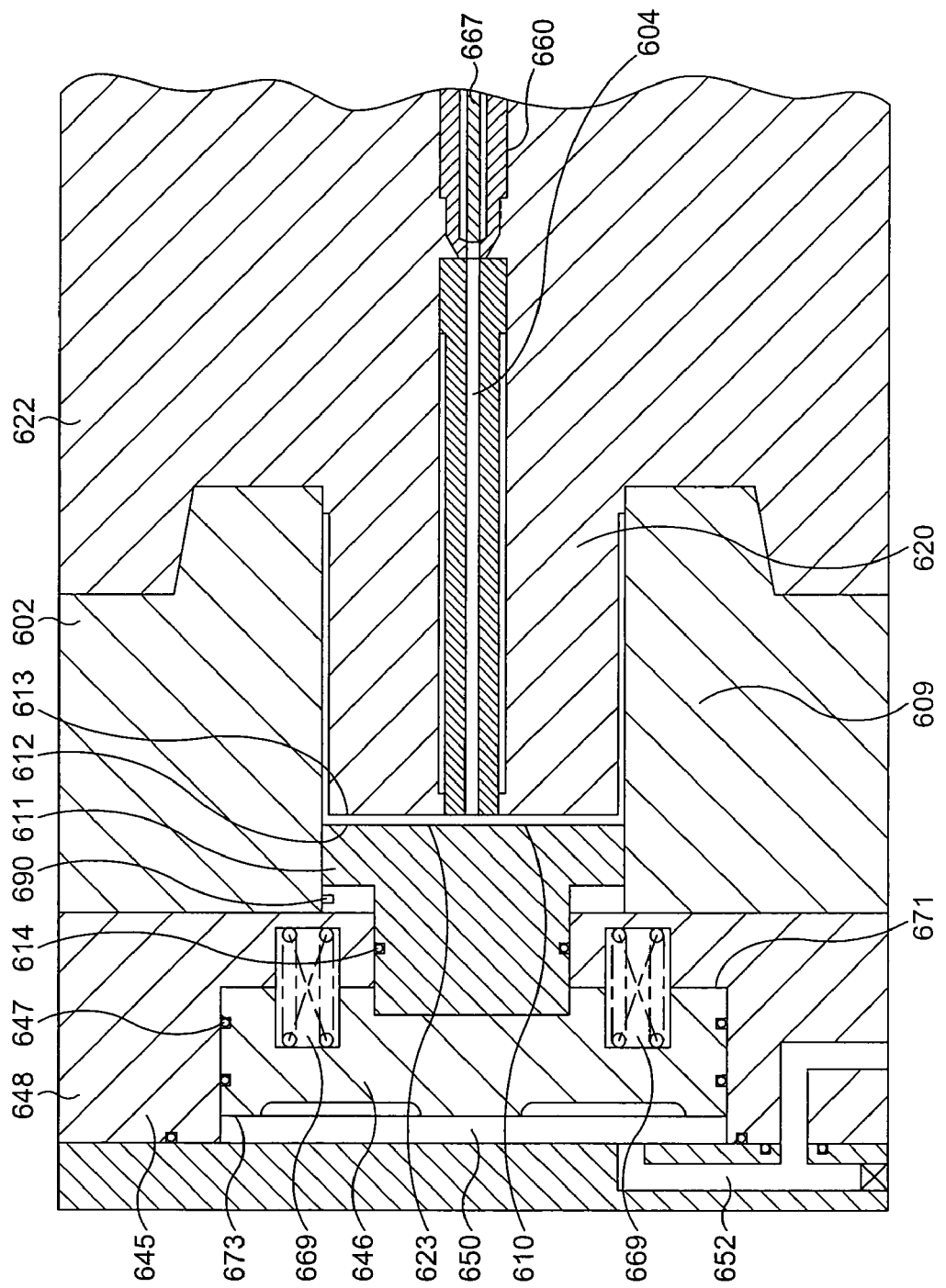
FIG. 8 is a schematic cross-section through an injection mould having a movable cavity part in accordance with a seventh embodiment of the present invention.

FIG. 8 is a schematic cross-section through an injection mould (602) having a movable cavity part in accordance with a seventh embodiment of the present invention. This provides a very cost effective and well engineered injection mould that has, in use, relatively moving parts at elevated temperature.

The mould (602) has a fixed core (620), integral with a core plate (622), and a feed nozzle (604) extends through the core plate (622) and through the core (620). The feed nozzle (604) opens into the cavity (610). The nozzle (604) is connected to a machine shut off nozzle (660). The shut off nozzle (660) includes a shut off pin (667) that can selectively close the nozzle (660). When the nozzle (660) is shut, this allows the machine to screw back without applying pressure. The nozzle shut off pin (667) is actuated by the injection moulding machine by sliding the shut off pin (667) forwards to shut off the flow and rearwards to open. This is normally done by a hydraulic actuator (not shown) mounted under the injection unit and using a rod or cable to pull a lever, which in turn moves the shut off pin (667).

A movable cavity part (609) surrounds the core (620) and is longitudinally movable to open and close the injection mould cavity (610). A reciprocable cavity base (611) is slidably mounted within the movable cavity part (609) and is connected to a piston (646) of a hydraulic piston and cylinder assembly (645). The base (611) has a moulding face (612) oriented toward the end moulding face (613) of the core (620). The base (611) moves within an annular bearing (614) in a cylinder part (648) of the hydraulic piston and cylinder assembly (645).

The piston (646) is arranged so that longitudinal movement of the piston (646) correspondingly causes longitudinal movement of the base (611) thereby to vary the volume of the cavity (610) when the mould (602) is closed by mating of the core plate (622) and the movable cavity part (609). The piston (646) includes an outer annular part (647) that is received within a hydraulic chamber (650) of the cylinder part (648) of the hydraulic piston and cylinder assembly (645). The hydraulic chamber (650) has a fluid inlet (652) on the side of the piston (646) remote from the cavity base (611) for connection to a source of pressurised hydraulic fluid (not shown) including a hydraulic pressure device (not shown).

The reciprocal movement of the base (611) under control of the piston (646) to vary the volume of the base part (623) of the mould cavity (610) after closure of the mould (602) is similar to the reciprocal movement of the movable cavity part (409) of the embodiment of FIG. 4.

It is obvious to the skilled engineer that close fitting metal parts of an injection mould are subject to expansion when heat is applied. The heat comes from the molten thermoplastic material that is injected into the mould prior to moving the cavity parts. This heat source causes the cavity parts to expand, which, in turn, can reduce the working clearance. This can cause the moving parts to seize and therefore require expensive repair work.

The embodiment of FIG. 8 provides a good engineering solution to keep all the mould parts relevant to the moving part at the same temperature. This is readily achieved by having an area of the cavity base (611) move, and by having the molten material injected through the core (620). This is because the area surrounding the cavity base (611) is substantial in mass and volume and allows for plenty of cooling channels (not shown) and other cooling means (not shown) well known to those skilled in the art.

In the case of the core pad moving within the end of the core, as described in the embodiments of FIGS. 4, 5 and 7, for example, it is easy to cool the pad but difficult to cool the narrow area surrounding the pad. This means the pad diameter needs to be minimised to allow sufficient thickness for cooling channels and other cooling means. This can compromise the process, as it is obvious that the bigger the pad, the less the flow restriction will be during compression. This is because the displacing material would be closer to the container sidewall.

Therefore, as described in the embodiment of FIG. 8, a moving cavity base pad, the same, or nearly the same width (which for a circular pad which is used when a round container is being manufactured is the diameter) as the inside of the cavity sidewall, is preferred for achieving higher heat removal and temperature equilibration.

Another advantage of this structure, as described in the embodiment of FIG. 8, is to overcome the engineering problem of supporting a heavy core, as used for the manufacture of larger containers. The core, to make a 20-liter pail, would have an overhanging weight of approximately 1.5 tonnes. Supporting this weight as the core moves during the process, to reduce bearing wear, is a major engineering problem. The obvious solution is a long bearing of approximately 5×diameter, which, in turn, would extend the non overhanging length of the core and act as a counter balance. However, this dramatically increases the overhanging weight on the moving platen of the moulding machine. It also increases the space required between the machine platens beyond that of current machines of a suitable clamp tonnage. It would be possible to add support for the core, or mould, from the machine tie bars or the machine bed but this adds cost and will make the mould machine specific. These problems are avoided by having a fixed core (620) in the embodiment of FIG. 8.

A further advantage of the mould as described in the embodiment of FIG. 8 is that the core (620) does not move in relationship to the cavity (610). This is of particular advantage when the injection moulded container has holes in the side, such as a laundry basket, or has handle fitments and/or tamper evident features that need the core and cavity to shut out against their surfaces, or, for example, the article is a carbonated soft drinks closure that has a "tear" band.

In this embodiment of FIG. 8, the hydraulic piston and cylinder assembly (645) acting as actuator for controlling the motion of the reciprocable cavity base (611) is used in conjunction with a simpler control system for the hydraulics of the piston and cylinder assembly (645). No pressure detector is employed. The movement of the piston (646) is controlled by a switch (690) which is activated when the cavity base (611) has moved back enough to allow sufficient material to flow into the cavity (610). This acts as a simple two-pressure system in successive phases.

In a first phase, a low hydraulic pressure, as a retraction force, is applied to the piston (646) urging the piston (646), and consequently the cavity base (611), towards the core (620) as the material is injected into the cavity (610). This is to control the flow of the incoming material and stop the cavity base (611) from moving back too fast causing gas entrapment and jetting. Mechanical compression springs (669) (e.g. helical compression springs) are mounted on the front of piston (646) and are biased against the cylinder part (648). The mechanical compression springs (669) function to ensure a low hydraulic pressure above a minimum threshold is achieved, because otherwise too low a hydraulic pressure, for example less than 10 bar, would be very difficult to control due to the resistance present, from the viscous hydraulic fluid, in the hydraulic control valves. Other spring biasing force structures and methods may alternatively be used, such as gas springs or an air cylinder or cylinders, or actuators to push against the hydraulic force that are de-activated when high pressure commences.

When sufficient plastic material has entered the cavity (610), the piston (646), and consequently the cavity base (611), have moved back a given distance, the switch (690) is mechanically triggered. The switch (690) switches the hydraulic piston and cylinder assembly (645) into a second phase in which a high hydraulic pressure as a forward force is applied in the opposite direction to urge the cavity base (611) forward. The switch (690) may have an adjustable position so that the switching between the first and second phases can readily be adjusted.

In the embodiments disclosed earlier herein in which the cavity volume is controlled by detecting and controlling pressure within the cavity, the rate of movement of the mould parts can readily be controlled by controlling the pressure. However, in this embodiment, in which the system and method are simplified by using one hydraulic supply and a switch to detect movement of a mould part, it is desirable to prevent the cavity/core part from shooting backwards in the initial phase at too high a retraction speed.

The leading edge of the molten material (melt front) needs to stay in contact with both sides of the mould. If the melt front is too thick it will have a rounded leading edge that will hit the cavity side wall and trap gas below it, in the bottom corner of the cavity. This will then diesel under compression and cause a black "smoky" burn mark up the side of the moulding. Another problem is jetting, which is when there is insufficient pressure at the gate to control the injection. The material would jet uncontrollably through the gate at high speed, leaving a snake like mark on the bottom of the moulding. The material needs to pass through the gate, against the core/cavity moving part, so that it stays in contact with the surrounding surfaces. If the gap between the gate and the core/cavity part is fixed then the area close to the gate needs to be controlled.

The projected area of the melt front is increasing as it flows across the core and cavity base parts, and therefore the hydraulic force from the flowing melt applied against these parts is increasing. This is why the method requires an initial backwards movement, achieved in practice by a low reaction pressure, to start with. The mechanical springs (669) help to achieve the desired low reaction pressure in a controlled manner so that the reaction pressure is controlled to be low but above a minimum threshold, since it is not possible to control the hydraulic fluid used in the system at very low pressure. Accordingly, the hydraulic piston (646), that applies the compression force against the cavity base (611), has a "sprung" biasing force applied to its front surface (671) by the springs (669) to urge the cavity base (611) away from the core (620) but in fact the main task of the springs (669) is to raise the oil pressure on the back (673) of the piston (646) to a minimum controllable level.

A similar control system instead of the pressure transducer can optionally be used with any of the other embodiments disclosed herein.

It is well known in high-speed injection moulding to inject the plastic resin before the mould has completely closed, or, as preferred by the machine manufactures for safety reasons, injection can take place as the locking force is applied. The moulds of the present embodiments of the present invention may be utilized so as to benefit from the cycle time savings of this technique by allowing injection to commence as the mould is closing but before the mould has become fully closed. However, the locking force on the mould needs to have established a minimum sufficient force before compression starts. Otherwise the compression force from the injected resin could overcome the machine locking force, thereby leaving the moulded container with an undesirably thick base.

For the avoidance of doubt, it should be understood that various features of the illustrated embodiments may be used interchangeably, and that other embodiments of the present invention may be provided using one or more combined features from two or more different embodiments.

This injection moulding method of the present invention uses a new technique referred to herein as Variable Displacement Moulding (VDM). The method enables a simple technology for processing thermoplastic materials to make, for example, containers, closures and lids. The injection moulded products are hollow articles that have a base and a sidewall extending upwardly therefrom. The articles may have any cross-sectional shape, for example they may be round with an axis of rotation about which the article is substantially rotationally symmetric (e.g. a preform for subsequent blow moulding to form a container such as a bottle, which is rotationally symmetric except for the threads on the neck finish, or a bucket which is rotationally symmetric except for two opposed handle mounts). Alternatively, the articles may have a non-round cross-section, e.g. square, elliptical, rectangular, and/or may have no symmetry.

The method can use any standard injection moulding machine. The injection mould design incorporates a movable portion, as discussed above, but otherwise employs a mostly conventional mould design and build. There is a simple mechanism, e.g., hydraulic, for varying the mould displacement. The controller provides an intelligent control system to optimise the injection moulding process, in particular by minimizing residual stress and melt pressure within the cavity. The embodiments of the present invention can typically provide an improvement in the L/T ratio by about 20% for the moving pad and 50% for the moving core or cavity, depending on the geometrical shape of the injection moulded article, and a reduction in the cavity fill pressures of about 25% to 50%.

The Variable Displacement Moulding method differs from conventional injection moulding as it allows the material to flow more freely into the cavity, therefore reducing pressures, temperatures and stress.

The Variable Displacement Moulding method also differs from injection compression moulding and sequential injection compression moulding as it does not use the clamp force of the injection moulding machine to flow the material throughout the cavity, nor does it need a precisely dosed shot weight, valve gate hot-runners or external guidance systems.

In preferred embodiments of the Variable Displacement Moulding method, at least a part of the core is allowed to move away from the incoming plastic material against a controlled force, or alternatively a part of the cavity base wall is allowed to move in the case of feeding the material through the core. In each case, this reduces the pressure in the gate area during the start of the fill phase. At the end of the fill phase (as the flow of material slows down) and the lower pressure packing phase starts, the core, or core part, or cavity wall part, is forced forward by an actuator, which also assists in maintaining the packing pressure.

When moving the core part or cavity base wall part back, there would be a tendency for the skin to solidify against the exposed sidewall surface left by the sliding part. To reduce this cosmetic problem, it would be desirable to have large area moving parts and to minimise the stroke distance of the moving part. To further reduce the skin thickness, it would be desirable to reduce the time between the start of the filling phase and when the moving part has completed its forward stroke. The ideal time would be when the incoming flow reduces in speed at the end of the filling phase. The filling phase of the Variable Displacement Moulding method may be made much shorter than convention injection moulding, due to the lack of flow restriction opposite the gate, and so the contact time will shorter and therefore the skin will be thinner.

The last part of the filling phase, or during the holding phase, the moving part returns to its forward position. This could be assisted by allowing material to pass back through the gate. As the moving part is only a proportion of the core, or cavity base, it would require less force to move it to its end position than moving the whole core or cavity base. This is because its projected area is reduced from that of the whole core. As the volume of the cylinder left by retracting the moving part is only about 25% of the total capacity required to completely fill the cavity, the stroke of the moving part can be minimised.

The force applied to the moving part needs to be sufficient to move the moving part forward against the holding pressure, typically 150-kgs/square centimeters.

It is envisaged that conventional injection-moulding machines, normally used for packaging applications, would be ideal for this Variable Displacement Moulding method of the present invention.

As there are moving parts in the core, or cavity base, it is desirable to have very close tolerances, surface finishes, and surface treatments, to minimise witness lines or vertical flash on the surface of the mouldings. The possibility of this detrimental appearance would, however be reduced since the cavity pressure would be lower than in conventional injection moulding processes.

In preferred embodiments of the invention, a hydraulic actuator is used to control the stroke of the pad, a transducer is placed in the pad (or in the oil supply) to monitor the pressure from the injected melt and a control unit is supplied to interpret the information. A proportional valve is mounted on, or near the mould with a constant pressure supply of hydraulic oil from the machine, or power pack. When the transducer senses the pressure rising above the set value, the hydraulic cylinder pressure is reduced to allow the pad to move back to increase the flow rate. As the filling pressure changes to the reduced holding pressure, the hydraulic pressure is increased, forcing the pad forward and assisting with the pack-out. If valve gates are used, the controller would close them at the optimum point in time.

For multi cavity applications, in preferred embodiments of the invention there may be a transducer in each pad feeding back to the controller. This would either control individual actuators, and therefore control the pressure balance of the mould, or calculate the mean and control a single actuator driving all of the pads. It would also be possible to individually control the valve gate bushings in sympathy with the flow into each cavity, should they be required. The Variable Displacement Moulding assists in the balancing of the material flow in multiple cavity moulds. The timing of the pad forward movement can be varied but the optimum should be just before the filling is completed, adding the pad force to help complete the flow of material.

The present invention therefore uses a fully closed mould and controls the variable cavity, for example by controlling the core to match the incoming flow of material. Otherwise, if the core movement is too slow, a high pressure is maintained in the gate area, or if the core movement is too fast this may cause air entrapment, gravitational effects and cavitation caused by the pressure drop after the material passes through the gate (known in the art as jetting).

The Variable Displacement Moulding method can use a hydraulic cylinder attached to the core and a pressure transducer to measure the injection pressure. There is an intelligent control system to interpret the information from the transducer and control the core movement. The core is allowed to move back against the fill pressure to keep it as low as possible and then move forward as the injection slows down. The core then maintains pressure on the material as well as the injection pressure.

The result is the lowest fill pressure to achieve a fully packed moulding with the minimum of stress.

It is believed by the present inventor that the present invention is able to achieve the lowest stress levels known today in preforms and other container type mouldings. It is possible to make longer, thinner preforms without increasing their residual stress levels. The low-pressure moulding method of the present invention can also reduce core shift problems. Cycle times can be much shorter due to the elimination of over pack (which could cause the preform to stretch on opening of the mould).

One particular advantage of the present invention is that by using an actuator for the moving mould part, in particular a hydraulic actuator in the form of a piston and cylinder assembly, this can permit very high velocity of the mould moving part to be achieved. In injection moulding, forward speed of the melt front is related to the L/T ratio. For very thin walled mouldings with a long flow path, a very high velocity of the melt front is required; otherwise the melt simply solidifies on the sides of the mould cavity and prevents the molten material reaching the more remote ends of the cavity. In accordance with the present invention, the actuator driving the moving mould part can achieve much higher melt front velocities than a conventional injection moulding machine can achieve. With the Variable Displacement Moulding method, the actuator can be operated, for example the when a hydraulic actuator is used the rate of supply of hydraulic fluid can be varied, to achieve whatever melt front velocity is required. It is possible using an actuator in accordance with the invention to achieve an L/T of up to or even over 1000:1, an improvement of 300% on known injection moulding technology, and to be able to injection mould walls having a thickness, for example 0.3 mm, thinner than has been achieved in a viable commercial injection moulding process to date.

The mould of the present invention is consistent with modern preform design with the additions of a sliding core, a hydraulic cylinder, pressure transducer and control system. The core actuator may be direct hydraulic with linear and pressure transducers to allow the controller to achieve the desired pressure profile. It would be obvious to the skilled person that other actuators can be used such as electronic, electrical or electro-mechanical actuators, or pneumatic actuators for lower pressure applications.

At the end of injection it is desirable not to let the core hesitate before moving forward as this may cause a shudder trace in the moulding. The core should preferably fluidly change direction and be moved forward under precise control. A profile of speed reduction, to compensate for the changing density of the material, should ideally be applied.

The Variable Displacement Moulding method of the invention can control the filling pressure by moving the core, or a part of the core, away from the gate. Increasing the base thickness opposite the gate, or close to, reduces the filling pressure.

For a very high aspect ratio article such as a PET preform, the movement is substantial at around 10 times final base thickness. In contrast, for a shallow container it could be as low as 2 to 3 times final base thickness.

This retracting movement serves two purposes, first to reduce the flow length to thickness ratio (Length over Thickness—L/T) and second, to reduce the fill pressure. In combination this can reduce filling pressures by as much as 70%, which would also allow much lower injection times due to the reduced resistance.

However, balancing low pressure filling in a multi cavity mould is more difficult as the hot runner system relies on a resistance pressure to balance against. Therefore, the movement needs to be controlled with a counter pressure. The counter pressure profile needs to start high to balance the hot runner pressure, relax to allow the material flow to increase and then increase nearing the end of fill to assist with displacing the material throughout the mould cavity. For single cavity moulds there will be no need for the high starting pressure.

It is not envisaged to use individual shot dose control per mould cavity but there are no reasons, other than cost and complexity, to exclude them within the scope of the invention. The retract pressure profile would simply match that of the displacement from the dosing system.

When the core, or core part, is moved forward against the material, the melt pressure maintained by the machine is increased to balance the increasing pressure within the mould cavity. This can act to either add more material to help completely fill the mould cavity or, allow some of the material to move back though the gate if the cavity pressure peak is too high. Either way the machine regulates the final mould cavity pressure.

Where shot dose control is used, a valve gate would be fitted to lock off the back flow from the mould cavity. The shot dose of material would be pre-determined by the dosing system and therefore not controlled from the machine.

The Variable Displacement Moulding method of the invention can balance the flow of material into the mould cavity by regulating the base wall section to reduce the filling pressure, and then balances the mould cavity packing pressure against the machine's injection pressure.

Filling of the mould cavity is improved by allowing faster injection times and the packing is improved by the forward speed and pressure being applied to a large surface area of the mould cavity instead of through a small gate.

A small amount of back flow through the gate can relieve gate stress. This is due to the displacement of the material that had been subjected to stress during filling. Gate temperature can also be drastically reduced due to the lower filling pressure; this can further reduce moulded in stress as the temperature affects the crystalline structure of the thermoplastic material, causing brittleness.

Peak fill pressure to pack out the end of flow can be controlled either by the displacement pressure of the core, or part of the core, or by the machine pressure.

It is possible to lock off the hydraulic flow from the actuator cylinder and use the machine to increase the pack pressure above that set by the moving core. However, this would greatly increase the pressure differential between the gate and the end of flow and therefore is not preferred.

The preferred method is to control the peak fill pressure by moving the whole core as this exerts pressure over the entire surface are, particularly in tapered containers where there is a crushing force applied throughout the side wall.

The compromise is the pad method where the majority of the end of the core is moved to create the largest possible annulus and therefore the minimum of flow restriction. This method is ideal when handle fitments and tamper evident features are shut out against the core. This is also the preferred method for making closures that have perforated skirts for tamper evidence.

Where the mould is fed through the core, to assist In Mould Labeling (IML), it would be necessary for the gate area to be fixed and allow the pad to move around it. Therefore the pad would have a hole in the centre with a close tolerance fit around the gate bush. It is also possible to move the cavity, or part, of in the same way.

Although various embodiments of the present invention have been described in detail, it will be apparent to those skilled in the art that other modifications of the injection mould and the injection moulding process may be employed that are within the scope of the invention as defined in the appended claims.

The invention claimed is:

1. A method of injection moulding an article having a base and a sidewall, the method including the steps of:
   (a) providing an injection mould comprising first and second mould parts;
   (b) disposing the first and second mould parts in a fully closed configuration so as to define a mould cavity therebetween, in the fully closed configuration the first and second mould parts defining a cavity outer surface which defines the outer shape of the article to be moulded in the mould cavity, the mould cavity having a base-forming portion and a sidewall-forming portion for respectively forming a base and a sidewall of an article to be moulded;
   (c) injecting molten material into the cavity at an injection inlet of the cavity; and
   (d) moving at least one portion of one of the first and second mould parts away from the injection inlet during the injection thereby to vary the volume of the mould cavity in the fully closed configuration,
   wherein in step (d) the moving of the at least one portion of one of the first and second mould parts away from the injection inlet during the injection controls the filling pressure of the molten material in the cavity according to a predetermined pressure characteristic in an injection moulding cycle, wherein the volume of the cavity is enlarged in a first phase of the injection moulding cycle and reduced in a second phase of the injection moulding cycle, in both of which phases the molten material is injected into the mould cavity, wherein in a third phase, following the second phase, of the injection moulding cycle the volume of the cavity is continued to be reduced, in which third phase the injection of molten material into the mould cavity has been terminated, and wherein at the end of the second phase the mould cavity is overfilled with the molten material and in the third phase any excess molten material in the mould cavity is urged back through the injection inlet against a controlled injection pressure.

2. A method according to claim 1 wherein the injecting step (c) is commenced during disposing step (b) as the first and second mould parts are being urged together under a locking force.

3. A method according to claim 1 wherein the filling pressure of the molten material in the mould cavity is controlled according to the predetermined pressure characteristic throughout the injection moulding cycle.

4. A method according to claim 1 wherein the pressure of the molten material in the mould cavity is reduced to a value below the injection pressure of the injector during a central portion of the injection moulding cycle.

5. A method according to claim 1 wherein in the third phase the molten material is packed under pressure in the mould cavity to accommodate any shrinkage of the injected material in the third phase.

6. A method according to claim 1 wherein the at least one portion of one of the first and second mould parts is moved towards and away from the other of the second and first mould parts so as to vary a separation distance therebetween, at a region of the mould cavity in the vicinity of the injection inlet.

7. A method according to claim 6 wherein the separation distance is varied by a factor of at least two times the width of the separation distance when the mould cavity has its minimum volume.

8. A method according to claim 1 wherein the at least one portion of one of the first and second mould parts comprises a movable segment of one of the first and second mould parts.

9. A method according to claim 1 wherein the at least one portion of one of the first and second mould parts comprises the entirety of one of the first and second mould parts.

10. A method according to claim 1 wherein the first and second mould parts are, respectively, male and female parts that define therebetween the mould cavity having the base portion and the sidewall which is annular and extends from the base portion.

11. A method according to claim 10 wherein the injector inlet opens into the base of the mould cavity.

12. A method according to claim 10 wherein the injector inlet is of an injector that extends through the male part.

13. A method according to claim 12 wherein the injector inlet is of an injector that extends through the female part.

14. A method according to claim 10 wherein the first mould part is an elongate core received in an elongate cavity defined in the second mould part.

15. A method according to claim 14 wherein the at least one portion of one of the first and second mould parts comprises a movable segment of one of the first and second mould parts and wherein the movable segment is a base part of the second mould part that faces a free end of the core.

16. A method according to claim 14 wherein the at least one portion of one of the first and second mould parts comprises a movable segment of one of the first and second mould parts and wherein the movable segment is a pad at a free end of the core.

17. A method according to claim 1 wherein the injection mould further comprises an actuator for selectively moving the at least one portion of one of the first and second mould parts in first and second directions so as to increase and reduce, respectively, the volume of the mould cavity.

18. A method according to claim 17 wherein the injection mould has a plurality of mould cavities each defined by a respective pair of the first and second mould parts, and each cavity having a respective injector inlet, and the actuator is a common actuator for simultaneously increasing and reducing, respectively, the volume of the plurality of mould cavities.

19. A method according to claim 17 further comprising controlling the direction of movement of the actuator.

20. A method according to claim 19 wherein the direction of movement of the actuator is controlled by a switch which is triggered by movement of the actuator or the at least one portion of one of the first and second mould parts to a particular position.

21. A method according to claim 19 wherein the direction of movement of the actuator is controlled by a detector for detecting a pressure associated with the actuator.

22. A method according to claim 20 wherein the detector is a pressure detector for detecting pressure applied to the actuator.

23. A method according to claim 17 wherein the actuator comprises a piston located in a cylinder and the piston is driven by pressurised fluid within the cylinder.

24. A method according to claim 23 wherein the detector comprises a pressure transducer for detecting fluid pressure within the cylinder.

25. A method according to claim 23 wherein the pressurised fluid is disposed in a chamber within the cylinder on one side of the piston.

26. A method according to claim 24 wherein the pressurised fluid is disposed in two chambers within the cylinder on opposite sides of the piston, and the pressure transducer detects fluid pressure in at least one of the chambers.

27. A method according to claim 17 wherein the actuator comprises a plurality of pistons, each located in a respective cylinder, and the plurality of pistons and cylinders are coaxially aligned in a longitudinal direction along the direction of movement of the pistons within the respective cylinders.

28. A method according to claim 1 wherein the mould cavity is adapted to mould a container or a preform for blow moulding into a container.

* * * * *